(12) United States Patent
Weeden

(10) Patent No.: US 9,192,478 B2
(45) Date of Patent: Nov. 24, 2015

(54) REVISION HIP IMPLANTS AND PROSTHESIS SYSTEMS

(75) Inventor: Steven H. Weeden, Fort Worth, TX (US)

(73) Assignee: Smith & Nephew, Inc., Memphis, TN (US)

( * ) Notice: Subject to any disclaimer, the term of this patent is extended or adjusted under 35 U.S.C. 154(b) by 211 days.

(21) Appl. No.: 13/698,406

(22) PCT Filed: May 18, 2011

(86) PCT No.: PCT/US2011/036999
§ 371 (c)(1),
(2), (4) Date: Nov. 16, 2012

(87) PCT Pub. No.: WO2011/146617
PCT Pub. Date: Nov. 24, 2011

(65) Prior Publication Data
US 2013/0066437 A1   Mar. 14, 2013

Related U.S. Application Data

(60) Provisional application No. 61/345,762, filed on May 18, 2010.

(51) Int. Cl.
*A61F 2/32* (2006.01)
*A61F 2/34* (2006.01)
(Continued)

(52) U.S. Cl.
CPC ... *A61F 2/34* (2013.01); *A61F 2/32* (2013.01); *A61F 2/3609* (2013.01); *A61B 17/1631* (2013.01); *A61B 17/1666* (2013.01); *A61B 17/1746* (2013.01); *A61B 17/8057* (2013.01); *A61B 17/8605* (2013.01); *A61B 17/8685* (2013.01); *A61B 2019/304* (2013.01); *A61F 2/30724* (2013.01); *A61F 2/30744* (2013.01); *A61F 2002/3055* (2013.01); *A61F 2002/3069* (2013.01); *A61F 2002/3092* (2013.01); *A61F 2002/30344* (2013.01); *A61F 2002/30449* (2013.01); *A61F 2002/30538* (2013.01);
(Continued)

(58) Field of Classification Search
CPC ..... A61F 2/32; A61F 2/34; A61F 2002/3611; A61F 2220/0033
USPC .......................................... 623/22.11–22.39
See application file for complete search history.

(56) References Cited

U.S. PATENT DOCUMENTS 5,217,499 A   6/1993   Shelley
5,571,198 A   11/1996   Drucker et al.
(Continued)

FOREIGN PATENT DOCUMENTS

DE   20 2005 020738 D1   8/2006
EP   0 958 797 A1   11/1999
WO   2009/081346 A1   7/2009

OTHER PUBLICATIONS

International Search Report, International Application No. PCT/US2011/036999, Mar. 20, 2012, 4 pages.
(Continued)

*Primary Examiner* — Jason-Dennis Stewart
(74) *Attorney, Agent, or Firm* — Taft Stettinius & Hollister LLP

(57) ABSTRACT

Revision hip implants and prosthesis systems include femoral heads, cups, screws, bridges, and segmental prostheses for revision surgeries.

14 Claims, 8 Drawing Sheets

(51) Int. Cl.
*A61F 2/36* (2006.01)
*A61B 17/16* (2006.01)
*A61B 17/17* (2006.01)
*A61B 17/80* (2006.01)
*A61B 17/86* (2006.01)
*A61B 19/00* (2006.01)
*A61F 2/30* (2006.01)

(52) U.S. Cl.
CPC ............... *A61F2002/30599* (2013.01); *A61F 2002/30604* (2013.01); *A61F 2002/30736* (2013.01); *A61F 2002/30774* (2013.01); *A61F 2002/3216* (2013.01); *A61F 2002/3401* (2013.01); *A61F 2002/3432* (2013.01); *A61F 2002/3446* (2013.01); *A61F 2002/3493* (2013.01); *A61F 2002/365* (2013.01); *A61F 2002/3625* (2013.01); *A61F 2002/3652* (2013.01); *A61F 2310/0073* (2013.01); *A61F 2310/0097* (2013.01); *A61F 2310/00796* (2013.01); *A61F 2310/00928* (2013.01); *A61F 2310/00976* (2013.01); *A61F 2310/00982* (2013.01)

(56) References Cited

U.S. PATENT DOCUMENTS

| | | | | |
|---|---|---|---|---|
| 6,416,553 | B1* | 7/2002 | White et al. | 623/22.38 |
| 2002/0147499 | A1 | 10/2002 | Shea et al. | |
| 2003/0171818 | A1 | 9/2003 | Lewallen | |
| 2005/0288793 | A1* | 12/2005 | Dong et al. | 623/22.28 |
| 2007/0142921 | A1* | 6/2007 | Lewis et al. | 623/22.36 |
| 2009/0210067 | A1* | 8/2009 | Meridew | 623/22.24 |
| 2010/0145466 | A1* | 6/2010 | Slone | 623/22.15 |
| 2010/0256771 | A1* | 10/2010 | Roberts et al. | 623/22.36 |

OTHER PUBLICATIONS

European Supplementary Search Report and Examination Report, European Patent Office, European Patent Application No. 11784169.2, Oct. 13, 2011, 12 pages.

* cited by examiner

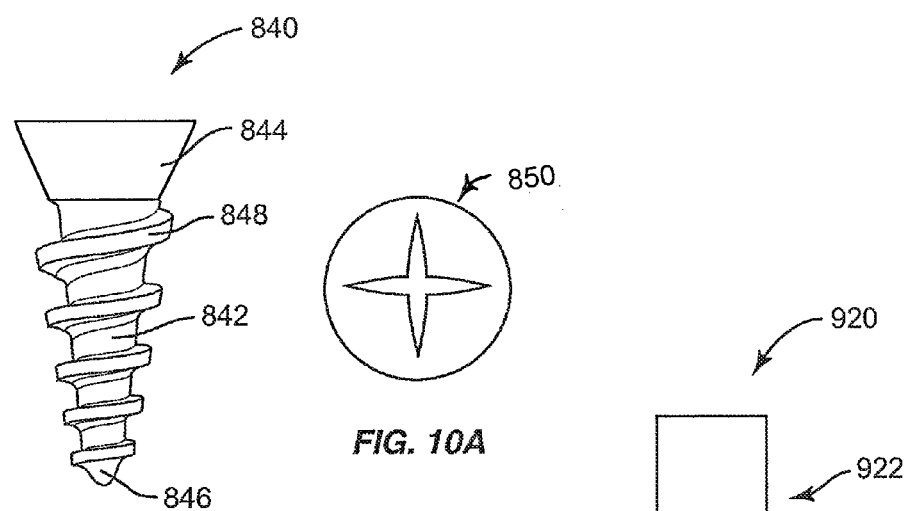
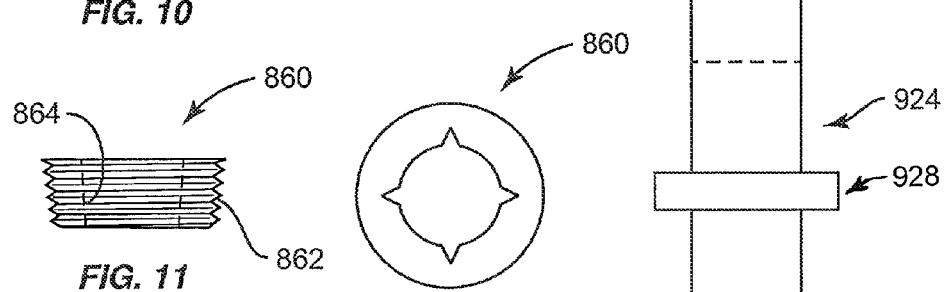
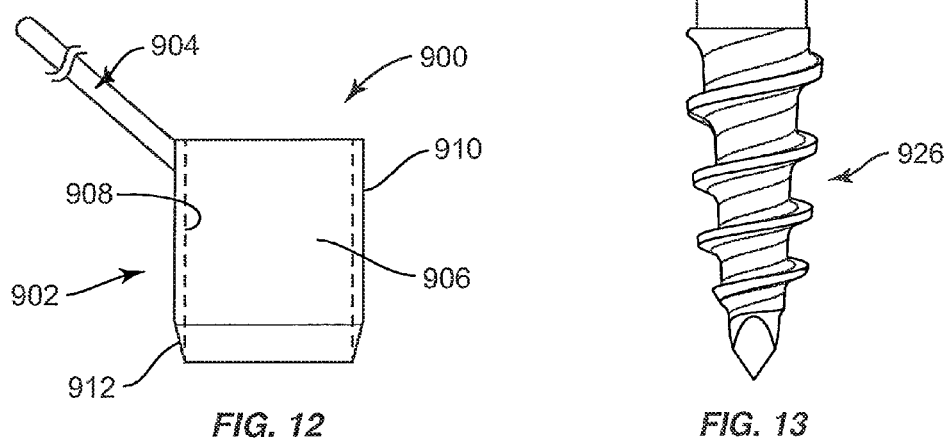

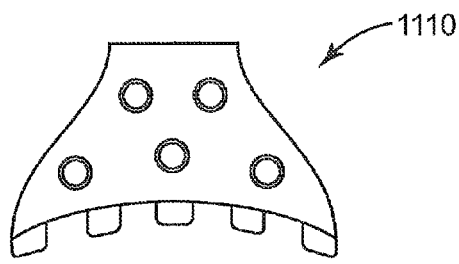
FIG. 18
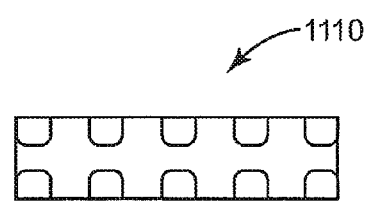
FIG. 19
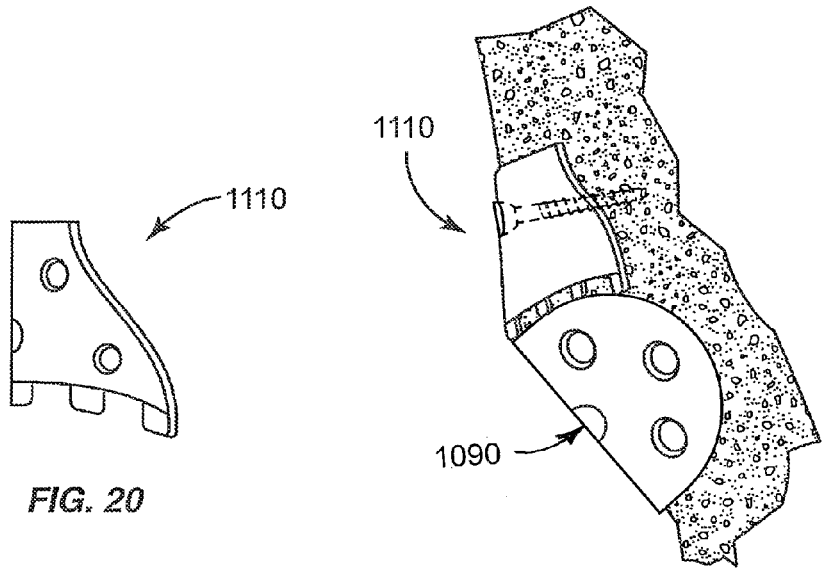
FIG. 20
FIG. 21

| CUP | LINER | HEAD |
|-----|-------|------|
| 72 | 64 | 58 |
| 70 | 62 | 56 |
| 68 | 60 | 54 |
| 66 | 58 | 52 |
| 64 | 56 | 50 |

REVISION HIP IMPLANTS AND PROSTHESIS SYSTEMS

CROSS REFERENCE TO RELATED APPLICATIONS

This application is a U.S. National Phase of International PCT Application No. PCT/US2011/036999 filed on May 18, 2011, which claims the benefit of priority of U.S. Provisional Application No. 61/345,762 filed on May 18, 2010, the contents of each application hereby incorporated by reference in its entirety.

FIELD OF THE INVENTION

The present disclosure is directed to revision implants and prosthesis systems, and more particularly, is directed to revision implants for hips and associated complex hip systems.

BACKGROUND

Hips are critical to mobility and overall lifestyle satisfaction for patients of all ages. However, hips can strain, rupture, degenerate, and break due to injury, degradation, previous surgery, disease or the like to such a degree that surgical correction becomes necessary. Often, the surgical correction includes the removal of the natural femoral head and replacement with prosthetic implants and replacing both the femoral head and the acetabular socket. It also often includes replacement of the natural acetabulum of the pelvis with a prosthetic acetabular cup.

In some cases, the implanted prosthetics may not function properly for any of a wide variety of reasons including, for example, failure of or damage to the implant, poor tissue healing, the deterioration of the function and/or shape of the supporting bone tissue, subsequent accidents, implant subsidence, pain, wear, premature loosening and/or other patient-related factors. In response, revision surgery, that is, another surgical correction may be required in which the implanted prosthetics are removed, replaced, or modified in the femur or pelvis.

Removal, replacement, or modification of an existing implant can be traumatic and painful for a patient. For example, it may require portions of bone to be resected, which in some cases may impair the structural integrity of the host bone in the femur and the pelvic socket. In other cases, the removal of old implants may disturb the bone stock and alignment required for standard (off the shelf) implants. This often results in reduced amounts of healthy tissue to work with during the revision surgery. Accordingly, revision surgery is often more difficult than the initial surgery because there is often less intact tissue, bone stock, and thinner bone structure, than was present during the initial surgery.

Although there continues to be improvements made to prosthetic hip implants and to revision techniques, a need remains for devices and systems that can more particularly maintain and support the surrounding bone tissue and support the patient's weight, activity, quality of life, while limiting patient trauma.

The implants and systems disclosed herein overcome one or more of the shortcomings of prior art devices.

SUMMARY

In one exemplary aspect, the present disclosure is directed to a tripolar revision hip implant for a revision surgery to revise a femoral head of a prosthetic femoral implant. The revision hip implant includes an inner layer of material formed of a polymer material and having a cavity therein. The cavity has a diameter in the range of 27-29 mm and has an opening with a diameter less than the diameter of the cavity. The opening is configured to receive the femoral head of the prosthetic femoral implant. The inner layer has an inwardly facing inner layer articulating surface configured to interface with and articulate with an outer surface of the femoral head of the prosthetic femoral implant. The revision hip implant also includes an outer layer of material surrounding the inner layer of material such that the inner layer is captured within the outer layer. The outer layer is formed of a hard, bearing carbide material, and has a curved articulating surface with a diameter greater than about 40 mm. The curved articulating surface is configured and arranged to interface with and articulate with boney structure of a patient's pelvic bone.

In another exemplary aspect, the present disclosure is directed to a method of performing a revision surgery. The method includes the steps of creating an incision in the patient in the region of the hip and accessing an original prosthetic femoral implant placed within the patient before the revision surgery. The original implant comprises a prosthetic femoral head of a prosthetic femoral implant. The method also includes placing a revision implant on the original implant, wherein the revision implant includes an inner layer of material formed of a polymer material and having a cavity therein. The cavity has a diameter in the range of 27-29 mm and has an opening with a diameter less than the diameter of the cavity. The opening is configured to receive the femoral head of the prosthetic femoral implant. The inner layer has an inwardly facing inner layer articulating surface configured to interface with and articulate with an outer surface of the femoral head of the prosthetic femoral implant. The revision hip implant also includes an outer layer of material surrounding the inner layer of material such that the inner layer is captured within the outer layer. The outer layer is formed of a hard, bearing carbide material, and has a curved articulating surface with a diameter greater than about 40 mm. The curved articulating surface is configured and arranged to interface with and articulate with boney structure of a patient's pelvic bone.

In some aspects, placing a revision implant on the original implant comprises placing the revision implant over the prosthetic femoral head in a manner that the prosthetic femoral head is disposed within the revision implant. In some aspects, the method includes enlarging a socket within the patient's pelvic bone; and inserting the revision implant into the enlarged socket in the pelvic region.

In another exemplary aspect, the present disclosure is directed to a revision hip implant bridge adaptor for extending between a femoral ball and a femoral stem on a prosthetic femoral implant. The bridge adaptor includes a head portion forming a conical taper and having a first longitudinal axis, a cap portion having an inner receiving feature formed as a conical taper and a second longitudinal axis, and a body portion extending between the head portion and the cap portion.

In some aspects, the first and second longitudinal axes are coaxial. In some aspects, the first and second longitudinal axes are angled relative to each other within the range of 1 and 25 degrees. In some aspects, the cap portion is configured to receive a conical head formed as a frustum on the femoral stem on a prosthetic femoral implant, the cap portion being configured to articulate about the conical head.

In another exemplary aspect, the present disclosure is directed to a revision implant system for a revision surgery on a hip area of a patient. The system includes an acetabular cup comprising a cup portion and a peripheral portion. The acetabular cup has a first surface configured to interface with the pelvic bone of the patient, and has a second surface facing away from the pelvic bone of the patient. At least a part of the second surface faces a femoral component of a hip implant. The acetabular cup includes a plurality of screw holes extending through the cup from the first surface to the second surface, the screw holes having a first diameter at the first surface and a second diameter at the second surface. The second diameter is greater than the first diameter. The plurality of screw holes have threaded inner surfaces. The system also includes a first screw having a shaft and a head, the shaft having a third diameter less than the first diameter of the screw hole. The head has a fourth diameter greater than the first diameter of the screw hole. The shaft has threads configured to engage the pelvic bone structure, and the head has threads formed thereon configured to engage the threaded inner surfaces of the screws holes in the acetabular cup.

In some aspects, the system includes a second screw having a shaft and a head. The shaft has a fifth diameter less than the first diameter of the screw hole and the head has a sixth diameter greater than the first diameter of the screw hole. The shaft has threads configured to engage the pelvic bone structure. The head is free of threads and is configured to be driven into the threaded inner surfaces of the screws holes in the acetabular cup.

In some aspects, the plurality of screw holes are a first plurality of screw holes formed in the peripheral portion of the acetabular cup, and the acetabular cup further comprises a second plurality of screw holes formed in the cup portion and extending from a first surface to a second surface. The second plurality of screw holes having a first diameter at the first surface and a second diameter at the second surface the second diameter being greater than the first diameter. The second plurality of screw holes having threaded inner surfaces.

In some aspects, the system includes a cup hole adapter having an outer threaded surface and an inner threaded surface, the outer threaded surface being configured to engage the threads of one of the second plurality of screw holes. In some aspects, the first screw is sized such that the threads on the head of the first screw engage the threads on the inner threaded surface of the cup hold adapter.

In some aspects, the system further comprises a revision screw having a tapered shaft and a head, the shaft having a third diameter less than the first diameter of one of the second plurality of screw holes, the head having a fourth diameter greater than the first diameter of one of the second plurality of screw holes. The shaft has threads configured to engage the pelvic bone structure. The length of the revision screw is no more than twice the width of the revision screw. In some aspects, the revision screw includes a thread axially extending about a shaft with a thread spacing between 2 and 4 mm. In some aspects, the system includes a drill guide and a drill bit, with the drill bit being configured to fit within the drill guide.

In another exemplary aspect, the present disclosure is directed to a method of performing a revision surgery. The method includes introducing an acetabular cup into a patient. The acetabular cup comprises a cup portion and a peripheral portion. The acetabular cup has a first surface configured to interface with the pelvic bone of the patient and has a second surface facing away from the pelvic bone of the patient. At least a part of the second surface faces a femoral component of a hip implant. The acetabular cup includes a plurality of screw holes extending from the first surface to the second surface. They have a first diameter at the first surface and a second diameter at the second surface, with the second diameter being greater than the first diameter, the plurality of screw holes having threaded inner surfaces. The method also includes introducing a first screw through one of the plurality of screw holes and into the pelvic bone of the patient. The first screw includes a shaft and a head, with the shaft having a third diameter smaller than the first diameter of the screw hole. The head has a fourth diameter larger than the first diameter of the screw hole. The shaft has threads configured to engage the pelvic bone structure. The head has threads formed therein and configured to engage the threaded inner surfaces of the screw holes in the acetabular cup. The method also includes driving the screw into the pelvic bone until the threads on the head engage the threads of the prosthesis such that the cup is secured onto the pelvic bone.

In some aspects the method includes introducing a second screw through one of the plurality of screw holes and into the pelvic bone of the patient, the second screw comprising a shaft and a head, the head being devoid of threads.

In another exemplary aspect, the present disclosure is directed to a kit comprising: an acetabular cup having a plurality of screw holes formed therethrough, the screw holes having threaded inner surfaces; a first set of screws having a shaft and a head, the first set of screws being configured to attach the acetabular cup to a pelvic bone structure, the first set of screws each having a head with threads formed thereon sized and shaped to engage the threaded inner surfaces of the acetabular cup; a second set of screws having a shaft and a head, the second set of screws being configured to attach the acetabular cup to a pelvic bone structure, the second set of screws each having a head devoid of threads formed thereon; a third set of screws having a shaft and a head, the third set of screws being configured to attach the acetabular cup to a pelvic bone structure, and having a diameter greater than the first and second set of screws; and a cup hole adapter having an outer threaded surface and an inner threaded surface, the outer threaded surface being configured to engage the threads of one of the second plurality of screw holes, the inner threaded surface being configured to engage the threads formed on the heads of the first set of screws.

In another exemplary aspect, the present disclosure is directed to a revision bone screw including a tapered shaft sized to fit through a hole in an acetabular cup and engage a pelvic bone, threads extending about the tapered shaft, the threads having a consistent height relative to the shaft. The threads are spaced along the shaft within a range of 2-4 mm. A head is disposed at a proximal most end and having a diameter. The total screw length is less than 3 times the screw head diameter.

In another exemplary aspect, the present disclosure is directed to a modular segmental prosthesis system for supporting an acetabular cup. The system comprises an inner surface and an outer surface. The inner surface configured to interface with the pelvic bone of the patient, and the outer surface faces away from the pelvic bone of the patient. A side of the system extends between the inner and outer surfaces and forms a cement fixation area configured to interface with the acetabular cup. The system includes a plurality of screw holes extending from the outer surface to the inner surface. The screw holes have a first diameter at the inner surface and a second diameter at the outer surface, with the second diameter being greater than the first diameter, the plurality of screw holes having threaded inner surfaces. A first screw has a shaft and a head. The shaft has a third diameter less than the first diameter of the screw hole, and the head has a fourth diameter greater than the first diameter of the screw hole. The shaft has threads configured to engage the pelvic bone structure. The head has threads formed thereon configured to engage the threaded inner surfaces of the screws holes in the acetabular cup.

In another exemplary aspect, the present disclosure is directed to a method of performing a revision surgery. The method includes introducing a modular segmental prosthesis into a patient. The prosthesis comprises an inner surface and an outer surface, with the inner surface configured to interface with the pelvic bone of the patient and the outer surface facing away from the pelvic bone of the patient. A side of the system extends between the inner and outer surfaces and forms a cement fixation area configured to interface with the acetabular cup. The system includes a plurality of screw holes formed from the outer surface to the inner surface. The screw holes have a first diameter at the inner surface and a second diameter at the outer surface, with the second diameter being greater than the first diameter. The plurality of screw holes having threaded inner surfaces. The method includes introducing a first screw having a shaft and a head, with the shaft having a third diameter less than the first diameter of the screw hole and the head having a fourth diameter greater than the first diameter of the screw hole. The shaft has threads configured to engage the pelvic bone structure, and the head has threads formed thereon configured to engage the threaded inner surfaces of the screw holes in the acetabular cup. The method also includes driving the screw into the pelvic bone until the threads on the head engage the threads of the prosthesis such that the prosthesis is secured onto the pelvic bone.

In another exemplary aspect, the present disclosure is directed to a hard bearing liner for a previously implanted acetabular cup having a socket with an inner radius, the liner being introducible in a revision surgery. The liner includes a cup body having an inner surface and an outer surface. The liner being sized and shaped for insertion into the previously implanted acetabular cup. The inner surface is arranged to interface directly with a femoral ball of a prosthetic implant and the outer surface being configured to face previously implanted acetabular cup. Surface features formed on the outer surface protrude from the outer surface. The surface features are configured to provide gaps therebetween for accommodating cement. The surface features forming a radius substantially matching the radius of the socket of the previously implanted acetabular cup.

BRIEF DESCRIPTION OF THE DRAWINGS

The accompanying drawings serve to exemplify some of the embodiments of this invention.

FIG. 10 is an illustration of a unique and novel large revision bone screw usable with the acetabular cup in FIG. 6 according to one aspect of the present disclosure.

FIG. 10A is an illustration of an exemplary screw cap usable with the acetabular cup in FIG. 6 according to one aspect of the present disclosure.

FIGS. 11 and 11A are illustrations of an exemplary cup hole adapter usable with the acetabular cup in FIG. 6 according to one aspect of the present disclosure.

FIG. 12 is an illustration of an exemplary drill guide usable with the unique large revision screw in FIG. 10 to place the revision screw in the acetabular cup in FIG. 6 according to one aspect of the present disclosure.

FIG. 13 is an illustration of an exemplary drill bit usable with the drill guide in FIG. 12 according to one aspect of the present disclosure.

FIG. 18 is an illustration of a front view of another exemplary modular segmental prosthesis according to one aspect of the present disclosure.

FIG. 19 is an illustration of a cement fixation area of the modular segmental prosthesis in FIG. 18 according to one aspect of the present disclosure.

FIG. 20 is an illustration of a side view of the modular segmental prosthesis in FIG. 18 according to one aspect of the present disclosure.

FIG. 21 is an illustration of the modular segmental prosthesis of FIG. 18 in place on pelvic bone with an acetabular cup according to one aspect of the present disclosure.

DETAILED DESCRIPTION

Figure 1:
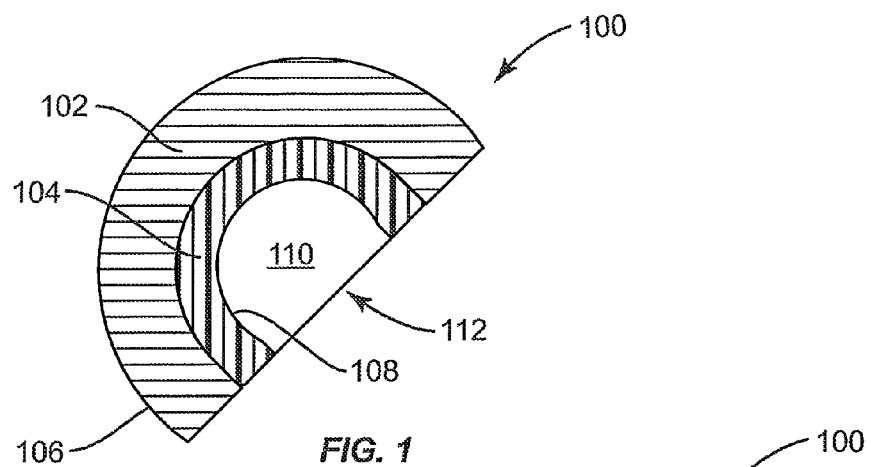
FIG. 1 is an illustration of an exemplary implant in cross-section according to one aspect of the present disclosure.

The present disclosure relates generally to the field of complex revision orthopedic hip surgery (arthroplasty), and more particularly to implants and systems for reconstructing a hip joint. In some aspects, the present disclosure is directed to revision devices for implantation after removal or modification of previously implanted prosthetic devices or to modify the previously implanted devices. For the purposes of promoting an understanding of the principles of the invention, reference will now be made to embodiments or examples illustrated in the drawings, and specific language will be used to describe these examples. It will nevertheless be understood that no limitation of the scope of the invention is thereby intended. Any alteration and/or further modifications in the described embodiments, and any further applications of the principles of these inventions as described herein are contemplated as would normally occur to one skilled in the art to which the disclosure relates.

This disclosure is directed to implants and implant fixation in complex revision hip arthroplasty surgeries. Revision hip surgeries are separate and distinct from initial surgeries to correct complex orthopaedic conditions. These revision surgeries typically correct, modify support, or exchange the original prior implants, including numerous fixation elements. However, removal or modification of the implants placed in a prior surgery can create even additional trauma and damage. Accordingly, revision surgeries often require additional consideration and complex techniques not commonly necessary during an initial surgery.

Some revision surgeries, and particularly, complex revision surgeries, require additional bone support due to damaged bone and trauma resulting from the original surgery and surgical or implant failure. The surgical implants and systems described herein may be particularly suited for revision surgeries, and therefore, may provide compensation and support for the previously implanted implant or device, making recovery easier and resulting in a better overall therapeutic and lasting result.

FIG. 1 shows an exemplary hip implant 100 that may be particularly suited for a revision surgery. In some embodiments, as described herein, the hip implant 100 is configured to interface with a previously implanted prosthetic femoral head. Accordingly, if the patient's acetabulum is worn or damaged, the hip implant 100 may be used between the patient's boney tissue and the previously implanted prosthetic femoral head.

The implant 100 is shown in cross-section and includes an outer layer 102 and an inner layer 104. Here, the outer layer 102 is formed of a hard bearing material, such as a high carbide cobalt material. In one example, the outer layer 102 is formed of a high carbon cobalt chrome. The outer layer 102 has a ball shaped articulation surface 106 particularly configured to engage and interface directly with boney tissue of a patient's natural acetabular cup or with an implant designed specifically for this material. Alternatively, if the natural acetabular cup is damaged or too small to contain the implant 100, then the ball-shaped articulation surface 106 interfaces directly with a socket formed and placed in the pelvis.

The inner layer 104 is formed of material having a hardness less than the bone-interfacing outer layer 102. In the embodiment shown, the inner layer 104 is formed of a polymer material, such as a polyethylene, although another polymer material may be used. In the embodiment shown, the inner layer 104 fits within the outer layer 102 in a manner that the two layers form a laminate and form a cavity 110. It includes an inner articulation surface 108. This surface is sized and arranged to interface with and articulate about a previously implanted prosthetic head that can be disposed within the cavity 110. In some embodiments, the cavity is dimensioned to receive and articulate about a 28 mm diameter prosthetic femoral head. To access the cavity 110, the implant 100 also includes an opening 112. The opening 112 may have a diameter smaller than the diameter of the cavity 110. In some embodiments, the opening 112 is dimensioned to have a 27 mm diameter, although other dimensions are contemplated. In addition, the outer layer 102 may have a diameter greater than 40 mm. In some embodiments, different sizes may be offered including sizes increasing from 40 mm in 2 mm increments.

Figure 2:
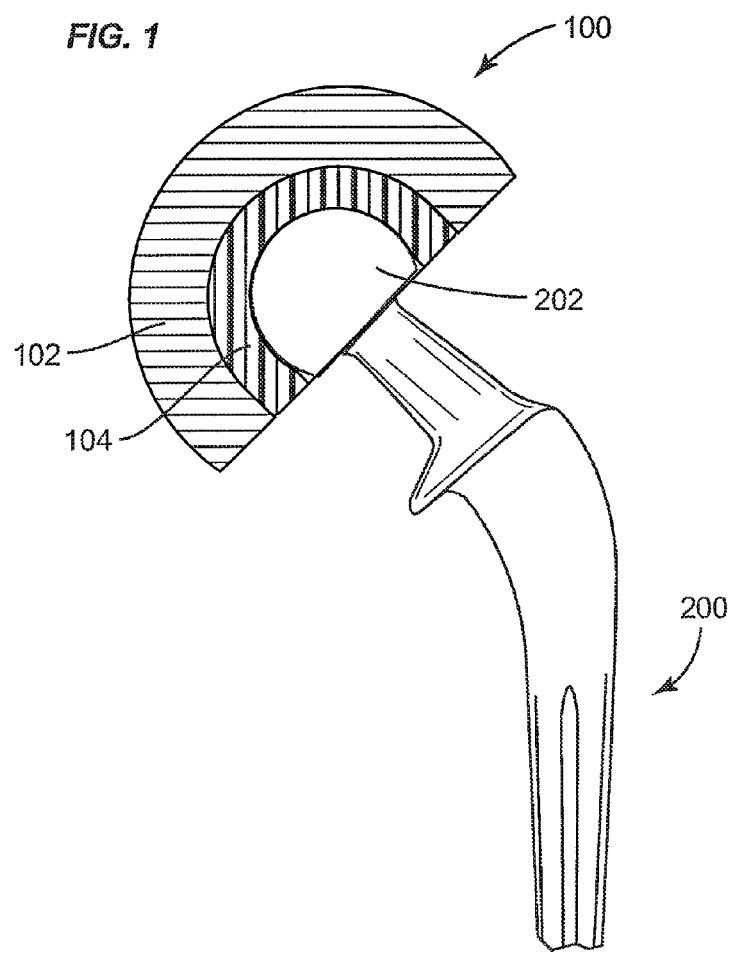
FIG. 2 is an illustration of the implant of FIG. 1 on a femoral prosthesis according to one aspect of the present disclosure with the implant placed on a host femoral implant.

FIG. 2 shows a partial cross-section of the implant 100 engaging a femoral implant 200 with a prosthetic femoral head 202. In some embodiments, the prosthetic femoral head 202 may have been previously implanted in a prior surgery, and the implant 100 is being applied to the prosthetic femoral head in a subsequent revision surgery. As can be seen, the prosthetic femoral head fits within the cavity 110 of the implant 100. Because the opening 112 is smaller than the diameter of the cavity 110, the implant 100 is secured onto the head 202, thereby reducing the chance of dislocation. In one example, the diameter of the femoral head 202 has a diameter about 28 mm.

When implanted, the inner articulation surface 108 articulates relative to the prosthetic femoral head 202. As discussed above, the outer articulation surface 106 articulates relative to the natural pelvic bone structure, possibly including a part of the natural acetabular cup. Accordingly, the implant 100 includes first and second articulation surfaces, making the implant 100 a tri-polar implantable device able to articulate with a compatible acetabular component.

Because the implant 100 is used to effectively increase the size of the femoral head that engages the pelvic bone, the implant 100 is more stable, and provides better functioning than the original prosthetic device. In addition, because the implant 100 is a tri-polar device, having two articulation surfaces, the device provides the following advantages of increased stability, decreased chance of dislocation, improved range of motion, and better hip function. Moreover, with this device a surgeon may be able to retain an older prosthesis yet provide the aforementioned advantages without major femoral revision surgery. Further, because the outer articulation surface is a hard bearing surface, the articulation surface does not provide for bone ingrowth, thereby providing a relatively smooth articulation and a potentially increased and longer lifespan.

In some embodiments, the outer diameter of the outer layer 106 is in the dimensional range of 40-64 mm. The thickness of the inner layer may be in the range of 4-8 mm, for example, and in some embodiments may be about 6 mm thick. Naturally, both larger and smaller thicknesses and sizes may be used.

In use, a surgeon may initiate a revision surgery to treat a problematic previously-placed implant, such as the prosthetic femoral implant 200. This may be because the implant 200 is failing, or alternatively, because the interfacing bone structure is not performing adequately. In some instances, it may be because of additional trauma, excessive loading, or simply patient discomfort.

In the surgery, the surgeon will commonly make an incision in the patient, and access the previously implanted device. After forming or treating the bone structure to create a sufficiently enlarged bony interface surface, the surgeon may connect the implant 100 onto the previously placed femoral head 202. In the embodiment disclosed, because the opening 112 is smaller than the outer diameter of the head 202, and smaller than the inner diameter of the cavity 110, the implant 100 may be forced over the head 202, causing elastic deformation of the inner layer 104, and snap-fitting the implant 100 onto the head 202.

The implant 100 may then be inserted into the newly enlarged socket in the pelvic bone. Accordingly, the implant 100 acts as a tripolar device, articulating with both the bone structure and the femoral head. This will provide an articulation and stability not achievable with the older technology.

Figure 3:
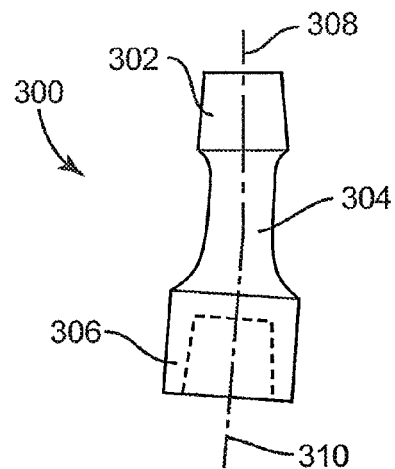
FIG. 3 is an illustration of an exemplary bridge adaptor implant according to one aspect of the present disclosure.

FIG. 3 shows one example of a femoral or acetabular offset/leg length bridge adapter 300. This adapter 300 finds particular utility when the hip is mismatched such that the hip articulation location is offset from the prosthetic femoral implant. FIG. 3 is a cross-sectional view of the bridge adapter 300. The bridge adapter 300 includes head portion 302, a body portion 304, and a female cap portion 306. A longitudinal axis 308 extends through the head portion 302. Similarly, a longitudinal axis 310 extends through the cap portion 306. In the example shown, the longitudinal axes 308, 310 are angled less than 8 degrees. This offset may provide better fitting for the patient, in view of the potential socket displacement due to damaged bone structure. In some embodiments, the longitudinal axes are coaxial.

Figure 4:
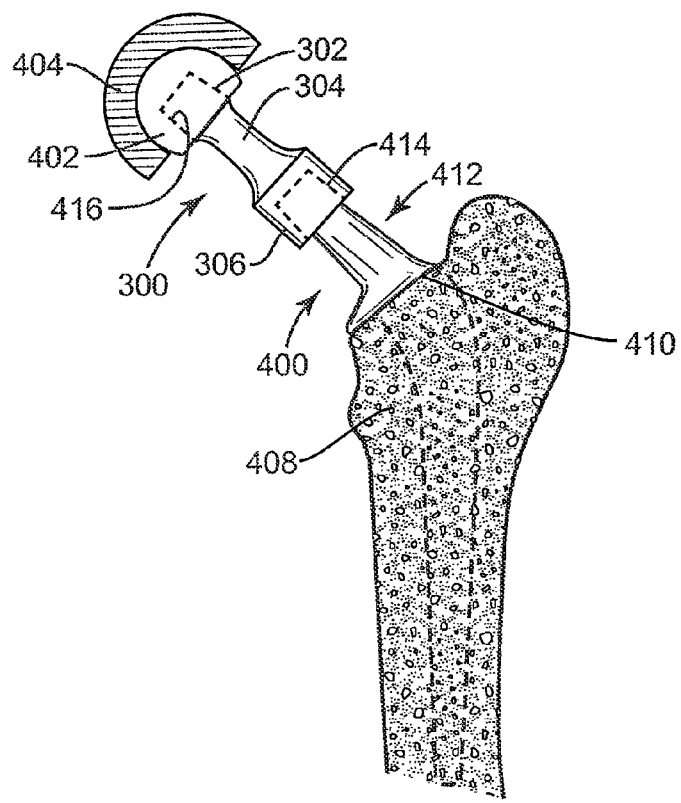
FIG. 4 is an illustration of the implant of FIG. 3 between a femoral stem and an acetabular ball according to one aspect of the present disclosure with the advantage of changing hip position.

FIG. 4 shows the bridge adapter in place as used with a patient. Particularly, FIG. 4 shows a prosthetic femoral implant 400, a prosthetic femoral ball 402, and an acetabular component 404. Here the bridge adapter 300 cooperates with the prosthetic femoral implant 400 and the prosthetic femoral ball 402 to bridge or extend the distance between them. The prosthetic femoral implant 400 is embedded within a femoral bone 408, and includes an engaging portion 410 for attachment to the femoral bone 408 and includes a femoral stem 412. The femoral stem 412 includes a head 414 receivable into the female cap portion 306. The head 414 and the femoral cap portion 306 each comprise conical tapered surfaces, such that the head 414 forms a frustum. In this embodiment, the taper of the head 414 is angled at the same angle as the head 302 of the adapter 300. Also, in some embodiments, the cap portion 306 is configured to articulate about the head 414 to thereby articulate about the longitudinal axis 310.

The head 302 fits within a corresponding opening 416 formed within the prosthetic femoral ball 402. The opening 416 is sized and shaped to receive the head 414, but because the head 302 and head 414 are similarly configured, the opening likewise receives the head 302. Accordingly, the adapter 300 effectively extends the distance between the prosthetic femoral implant 400 and the prosthetic femoral ball 402. Further, it provides angulation when desired to provide a better effect and more effective treatment.

The bridge adapter may find particular utility when damage or trauma to the acetabular cup is so extensive that the acetabular component must be placed at a new and deeper location in the pelvic bone. The adapter therefore will effectively extend the existing femoral stem, such as the stem implanted during a previous surgery or cancer bone destruction.

Figure 5:
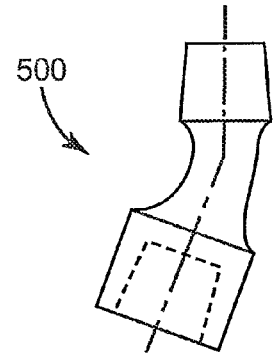
FIG. 5 is an illustration of another exemplary bridge adaptor implant according to one aspect of the present disclosure.

FIG. 5 is another example of a bridge adapter, referred to herein by the reference numeral 500. This adapter differs from the adapter referenced above in that the angle between the longitudinal axes 310, 312 is more pronounced. That is, the angle may be 25 degrees or less, for example.

When used in a revision surgery, the surgeon makes an incision in the patient, and accesses the previously implanted device. Instead of removing the previously implanted femoral implant, the surgeon may remove the previously implanted prosthetic femoral ball from the existing femoral stem. He may then implant the adapter onto the stem and place the prosthetic femoral ball onto the adapter head portion. The acetabular component may also be implanted or adjusted so that the femoral ball articulates in the acetabular component. This may provide a tremendous advantage in cases of bone carcinoma or complex acetabular/pelvic bone loss.

Figure 6:
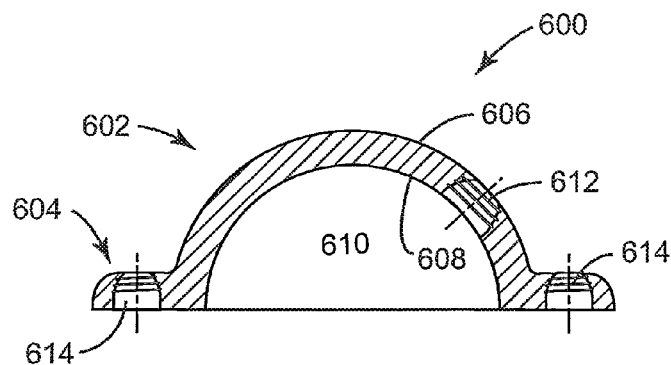
FIG. 6 is an illustration of an exemplary acetabular cup according to one aspect of the present disclosure.
Figure 7:
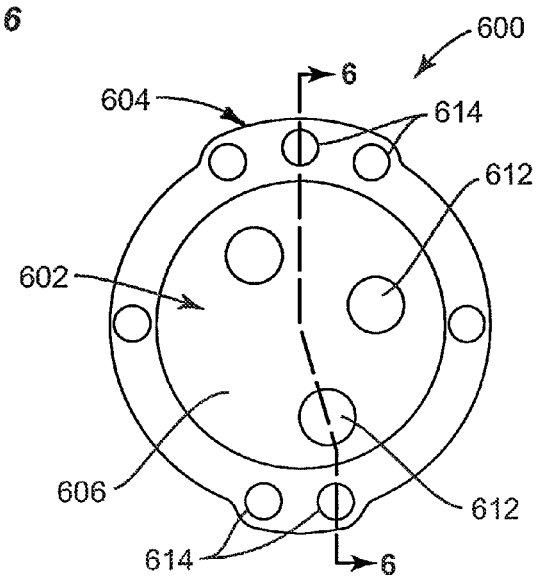
FIG. 7 is an illustration of the acetabular cup in FIG. 6 according to one aspect of the present disclosure.

FIGS. 6 and 7 show different views of a revision acetabular shell 600 with locking screws. FIG. 6 shows a cross sectional view of the shell 600 taken along the lines 6-6 in FIG. 7. FIG. 7 shows a top view, looking down onto shell 600. In this embodiment the acetabular shell 600 includes a cup portion 602 and a peripheral portion 604. The cup portion 602 includes an outer bone engaging surface 606, an inner ball engaging surface 608, and a hollow interior 610 formed by the inner ball engaging surface 608 and configured to receive a femoral ball or head.

In some embodiments, the cup portion 602 is formed of a porous material intended to provide for and promote boney ingrowth to help secure the shell 600 in place. Some embodiments include coatings that assist with and promote such boney ingrowth. For example, some suitable coatings include collagen-based coatings, bioceramic materials, such as BIO-GLASS®, hydroxyapatite and calcium phosphate compositions. Osteointigration compositions may be applied as a coating that include an effective amount of a bone morphogenetic protein, transforming growth factor β1, insulin-like growth factor 1, platelet-derived growth factor, fibroblast growth factor, LIM mineralization protein (LMP), and combinations thereof or other therapeutic or infection resistant agents, separately or held within a suitable carrier material. In revision surgery, one may consider the coating of antibiotics.

The cup portion 602 includes a plurality of through holes 612 configured to receive revision screws as described further below with reference to FIG. 10. Here, the holes 612 have a diameter greater at the top than at the bottom. Accordingly, in the embodiment shown, the holes are not cylindrical, but may be tapered or may have a curved inner surface. As shown in FIG. 6, the through holes have internal threads that are configured to engage threads on a screw or on an adapter as described below.

The holes 612 are sized with a large diameter, possible having a minimum diameter of about 7-9 mm, although other dimensions are contemplated. These large diameter holes enable large revision screws to be driven through, but also permit easy insertion of grafting material or bone growth materials into the regions between the shell 600 and the bone tissue.

The peripheral portion 604 is formed as a flange extending about the cup portion 602 and also comprises a plurality of through holes 614 configured to receive screws as described further below with reference to FIGS. 8 and 9. Like the through holes 612 described above, the holes 614 have a diameter greater at the top than at the bottom. Also like the through holes 612, the through holes 614 include internal threads. In the example shown, these holes 614 are threaded 5.5 mm angulating screw holes.

Figure 8:
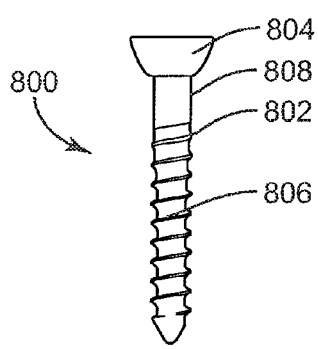
FIG. 8 is an illustration of an exemplary bone screw usable with the acetabular cup in FIG. 6 according to one aspect of the present disclosure.
Figure 9:
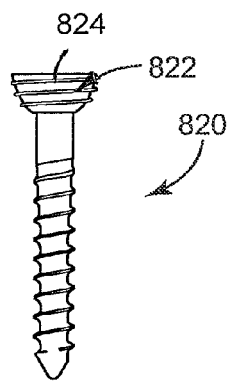
FIGS. 9 and 9A are illustrations of an exemplary bone screw with locking screw technology usable with the acetabular cup in FIG. 6 according to one aspect of the present disclosure.

FIGS. 8 and 9 show two examples of bone screws usable with the acetabular cup 600. These screws are configured to be inserted through the holes 614, and therefore, are 5.5 mm screws. It should be noted that these sizes are examples only and that other sizes are contemplated. FIG. 8 shows a screw 800 having a shaft 802 and a head 804. The shaft has a threaded portion 806 and an unthreaded portion 808. The threaded portion 806 is configured to engage and secure into bone tissue. The head 804 is conventional and is configured to engage within the screw hole 614 in the peripheral portion. Accordingly, while the shaft 802 has a diameter smaller than the diameter of the bottom of the screw hole 614, the head has a diameter greater than the bottom of the screw hole 614. The threaded proximal end of the screw is designed to provide rigid cup fixation and limit micro motion of the cup while bone osteointergration occurs over the first 6 months after revision hip surgery.

Figure 9A:

FIG. 9 shows a locking screw 820 an alternative screw. It is similar in many respects to the screw 800 in FIG. 8, but includes a head 822 with threads 824 formed thereon. The threads 824 are configured to engage and mate with the threads in the holes 614 in the peripheral portion 602 of the acetabular cup 600, thereby locking the screw to the cup. In this embodiment, the screws are configured to angle up to, for example, 20 degrees within the hole 614. This provides the surgeon with additional range of driving direction so that he can direct the screws into areas that appear to have the greatest purchase. FIG. 9A shows an exemplary driver interface shape. Other driver interface shapes are contemplated.

Although the threads engage and mate with the threads in the hole 614, in order to provide additional range of driving direction, the threads will only engage after the appropriate angle is chosen.

FIG. 10 shows a revision screw 840 sized for penetrating into the large screw holes 612 in the cup portion 602. The screw 840 includes a shaft 842 and a head 844, with the head 844 having a diameter larger than the shaft 842. In this instance, the shaft 842 is tapered from a distal tip 846 to the head 844. A thread 848 extends about the shaft 842. In this embodiments, the thread 848 projects from the shaft surface a relatively consistent amount over the course of the shaft. Accordingly, as shown in FIG. 10, the threads project from the shaft 2 mm. In this embodiment, the screw 840 comprises a single spiraling thread 848 spaced between 2 and 4 mm apart per revolution. Some examples have the spacing about 3 mm apart per revolution.

In the embodiments shown, the screw length is twice the head width. Here, the screw length is 20 mm and the head width is 10 mm. Similarly, the diameter of the shaft 842 and thread 848 adjacent the head 844 is nearly half the length. Accordingly, the screw 840 is relatively short and thick compared to conventional screws. This size ratio, and the ratios calculatable from the dimensions shown, enable the screw 840 to engage and secure in relatively thin bone tissue while securely holding the acetabular cup in place. In this manner, the screws may be particularly suited for complex revision surgeries where the bone tissue for attaching the acetabular cup is limited. This should provide maximum fixation in complex revision as never demonstrated with previous technology. In some examples, the revision screw 840 is formed of a porous material to promote bone ingrowth. It may also include any of the coatings described herein.

FIG. 10A shows an exemplary screw cap 850. The screw cap 850 may be used to close the holes 612 either after the screw 840 is driven through, or alternatively, may be used to close or plug the screw holes 612 after placement of bone, osteogenic, or growth promoting factors through the bone holes. Some exemplary bone and growth promoting factors include graft material, tissue, or other osteogenic materials that promote bone growth. Osteogenic materials include, without limitation, autograft, allograft, xenograft, demineralized bone, synthetic and natural bone graft substitutes, such as bioceramics and polymers, and osteoinductive factors.

Where longer screws may be desired or suitable, the system includes a cup hole adapter 860 shown in FIG. 11. This adapter 860 is configured to fit within the hole 612 in the cup portion 602, effectively changing the size of the hole 612 to receive more conventional screw types. As can be seen, the adapter permits a smaller sized screw, such as a 5.5 mm screw as described herein, to fit within the larger hole 612. The design promotes the use of the larger screws, yet in less complex cases the surgeon may choose to utilize the adapter and a 5.5 mm screw.

The adapter 860 comprises an outer threaded surface 862 and an inner threaded surface 864. The outer threaded surface 862 is configured to engage the threads in the hole 612. The inner threaded surface 864 is configured to receive one of the screws discussed above with reference to FIGS. 8 and 9. For example, when the locking screws 820 in FIG. 9 engage the inner threaded surface 864, the cup locks to the screws. Accordingly, the inner threaded surface 864 may be configured similar to the holes 614 formed in the peripheral portion 604. FIG. 11A shows a top view of the adapter 860. As can be seen, the adapter 860 includes features configured to engage a driver to tighten the adapter 860 in the hole 612.

FIGS. 12 and 13 show a drill guide 900 and drill bit 920, respectively. The drill guide 900 includes a cylindrical guide portion 902 and a handle 904. The handle 904 is offset from the guide portion 902 so that a surgeon will have clear access to the guide portion 902. The guide portion 902 is sized and arranged to interface with the holes 612 in the acetabular cup 600. The embodiment shown includes a cylindrical tube 906 having an inner diameter 908 sized to correspond with an inner diameter of the hole 612. In one example, this inner diameter 908 is 9 mm. An outer diameter 910 is sized to correspond to the diameter of the screw diameter, and in this example, is 10 mm. A tapered end 912 connects the inner and outer diameter surfaces. In this embodiment, the tapered end is shaped to correspond with the angle of the hole 612. Accordingly, when placed, the drill guide 900 aligns with the hole 612. The drill guide 900 has a height of 12 mm that corresponds with the drill bit 920 as discussed below.

The drill bit 920 shown in FIG. 13 cooperates with the drill guide 900 to create holes in the bone for receiving the screws. The drill bit 920 includes a flexible shaft 922, a central shaft 924, and a tapered drilling portion 926. The flexible shaft 922 is configured to interface with a drill (not shown) in a conventional manner. The central shaft 924 also includes a drill depth stop 928. The depth stop 928 is configured to engage the drill guide 900 to limit the distance the drill extends beyond the acetabular cup, and likewise, limit the distance the drill extends into the bone. The tapered drilling portion 926 forms the distal end of the drill bit 920 and is configured to displace the bone material. In the example shown, the tapered drilling portion is configured to match the bone screw 840 in FIG. 10, but may be dimensionally smaller. Accordingly, the drill bit 820 is configured to drill holes for the revision screw 840. In the embodiment shown, the tapered drilling portion 926 has a height of 19 mm, and tapers to a maximum width of 8 mm. The distance between the distal drilling portion and the depth stop 928 corresponds to the height of the drill guide. In this example, it is 12 mm.

In use, a surgeon may form a cavity in the pelvic bone in the area of the natural acetabular cup. The acetabular cup 600 may then be placed in the cavity. To secure the cup 600 in place, the surgeon may choose to drive securing screws through the holes 612 in the cup portion 602 and the holes 614 in the peripheral portion 604. In some embodiments, the surgeon may first secure the cup 600 using the screws 800, 820 in the holes 614. In some examples, the surgeon may use screws 800 in a first hole 614 or holes 614, without the threaded head, to pull the cup tight against the bone. Then, the surgeon may use locking screws 820 in additional holes 614 to lock the cup 600 fast in place. Because the screw heads thread into the cup structure itself, the locking screws 820 more securely lock the cup 600 to the bone structure. This technology is not currently utilized in revision hip surgery.

Accordingly, micro motion of the cup 600 relative to the pelvic bone structure caused by movement of a femoral ball is decreased or eliminated. This helps hold the cup 600 more securely, providing greater support and increased longevity. In other methods, the surgeon may use only the locking screws 820.

With the cup 600 held in place by the screws in the peripheral portion 604, the surgeon may determine the desired strategy for further securing the cup 600 or treating the bone structure behind the cup 600. In some embodiments, the surgeon may introduce graft, bone growth promoting materials, or other materials through the holes 614 formed in the cup portion 602 of the cup 600. After introducing such material, the surgeon may use caps that screw into the holes to close the holes. Alternatively, the surgeon may use the drill guide 900 and drill bit 920 to create holes for receiving the large revision screws 840. The large revision screws 840 have a length and width particularly suited to revision surgery because they are configured to provide superior holding without excessive length. Further, they provide improved fixation in difficult and compromised host bone.

Alternatively, the surgeon may determine that additional screws, such as locking screws 820 may be utilized to further secure the cup 600 in place. Accordingly, the surgeon may introduce a cup hole adapter 860 to the hole 612, and then introduce the locking screw 820 to the adapter 860.

Figure 14:
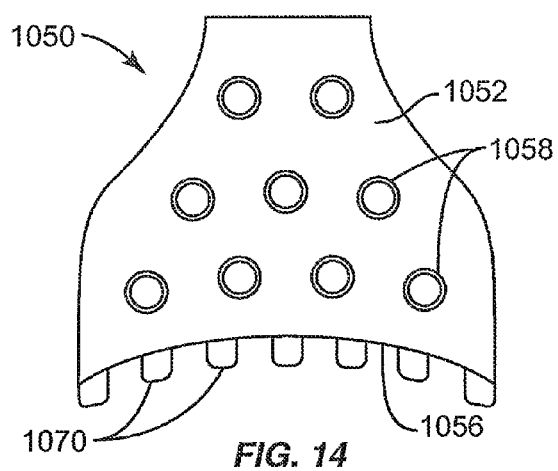
FIG. 14 is an illustration of a front view of an exemplary modular segmental prosthesis according to one aspect of the present disclosure.
Figure 15:
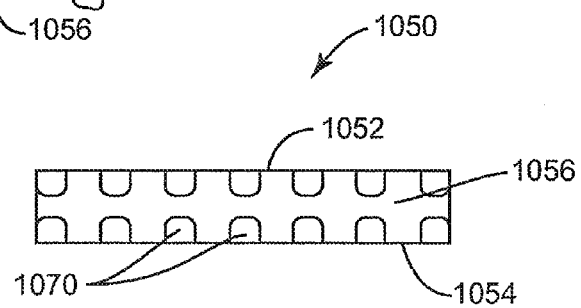
FIG. 15 is an illustration of a cement fixation area of the modular segmental prosthesis in FIG. 14 according to one aspect of the present disclosure.
Figure 16:
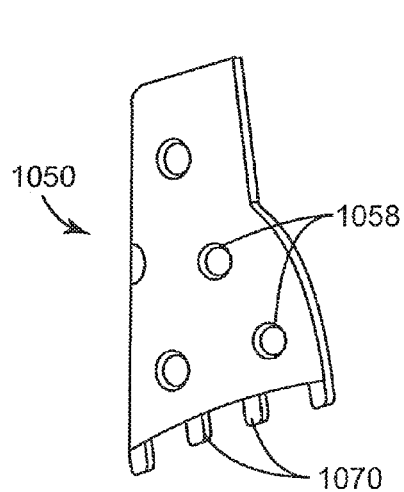
FIG. 16 is an illustration of a side view of the modular segmental prosthesis in FIG. 14 according to one aspect of the present disclosure.
Figure 17:
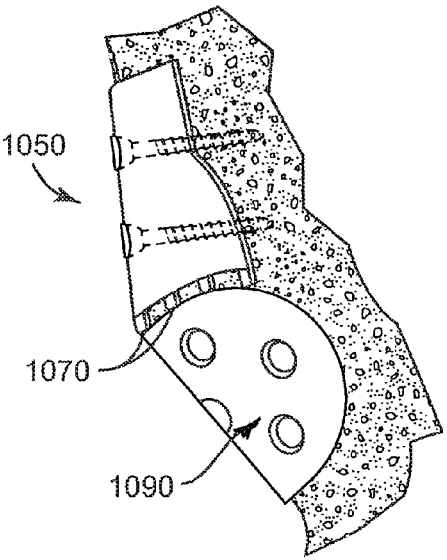
FIG. 17 is an illustration of the modular segmental prosthesis of FIG. 14 in place on pelvic bone with an acetabular cup according to one aspect of the present disclosure.

FIGS. 14-17 show an exemplary embodiment of a modular segmental prosthesis 1050. The prosthesis 1050 is configured to provide additional support to the acetabular cup when the bony structure is compromised. Accordingly, the prosthesis 1050 may be employed when the pelvic bone structure itself is insufficient to support an acetabular cup. FIG. 14 shows a front view, FIG. 15 shows a bottom view, FIG. 16 shows a side view, and FIG. 17 shows the prosthesis 105 implanted adjacent a prosthetic cup 1090 in boney tissue.

Referring to the FIGS. 14-17, the prosthesis 1050 includes an outer facing surface 1052, an inner facing surface 1054 (FIG. 15), and a cup fixation area 1056. The outer facing surface 1052 may be convex and configured to replace the outer surface of the compromised bone. An array of screw holes 1058 in the outer facing surface 1052 extends inwardly to the inner facing surface 1054. The screw holes 1058 are configured in the manner as the screw holes 614, with internal threads configured to engage locking screws having threads on the head portion. Accordingly, the holes 1058 will not be described in greater detail here. As can be seen, the holes 1058 are formed in an array, with more screws holes at the bottom and fewer screws holes at the top. These additional screw holes at the bottom may align with the compromised bone structure, and may be used to provide additional screws for additional support to the pelvic bone.

The inner surface 1054 may be concave shaped in cross-section, and it engages the bone structure. Accordingly, it may be treated with coatings or growth promoting factors to increase fixation to the bone. In one embodiment, hydroxyapatite may be used. Other materials may be used, including those described above. Further, in order to promote ingrowth, the segmental prosthesis is formed of materials with porosity greater than that of the acetabular cup 1090. In this example, the porosity is two times that of a standard acetabular cup. This provides a scaffolding for ingrowth and ongrowth.

The cement fixation surface 1056 includes a series of spaced protrusions 1070 configured to abut against the acetabular implant, but also configured to form gaps into which cement may be applied to cement the prosthesis 1050 to the acetabular cup. Accordingly, as shown in FIG. 17, the prosthesis 1050 and the cup 1090 may be cemented to each other.

After being cemented to each other, screws such as those disclosed in FIGS. 8 and 9 may be introduced. As described above, some techniques include introducing screws with unthreaded heads first to pull the prosthesis tight against the bone, then using the locking screws with the threaded heads to secure the prosthesis in place to avoid the micro motion or other degrading effects that may occur under cyclic loading with traditional screws.

FIGS. 18-21 show a small modular segmental prosthesis 1110. Since the prosthesis 1110 includes the screw holes and cement fixation area described above, its description will not be repeated here. As can be seen, the prosthesis 1110 is smaller than the prosthesis described above, and may be utilized when less support is necessary.

FIGS. 22-26 show a cementable hard bearing revision acetabular liner 1130 according to one aspect of the present invention. In some instances, previously implanted acetabular cups may be suitable as a backing for the liner. Accordingly, in a revision surgery, without removing the previously implanted acetabular cup, the cup may be revised by introducing the liner 1130 as the new liner. Doing so permits a new articulating surface without disrupting the bone-cup interface from the original surgery. In other instances, the liner may be implanted in new acetabular cups shell to provide a hard articulation surface. The liner 1130 forms the inner articulating surface of the acetabular cup. In some embodiments, it is formed of a hard bearing material that may include, among other materials, a high carbon carbide material. In some embodiments, the liner 1130 is formed of cobalt chromium. In other embodiments, the liner 1130 is formed of a ceramized zirconium (Trademark OXINIUM material by Smith & Nephew, Inc.).

Because it is shaped to fit within an acetabular shell, the liner 1130 is formed with an outer facing surface 1132 and an inner facing surface 1134. The inner facing surface 1134 defines a hollow cavity 1136 that acts as a socket for a femoral ball of the prosthetic joint. The outer facing surface 1132 is configured to be cemented to an acetabular shell to form the acetabular cup.

Figure 22:
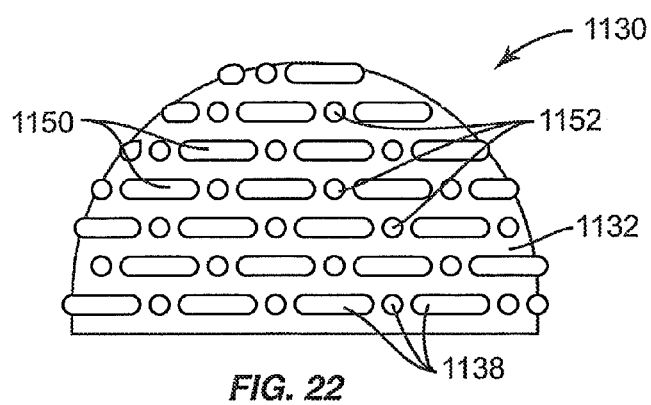
FIG. 22 is an illustration of a side view of an exemplary cementable hard bearing revision acetabular liner according to one aspect of the present disclosure.
Figure 23:
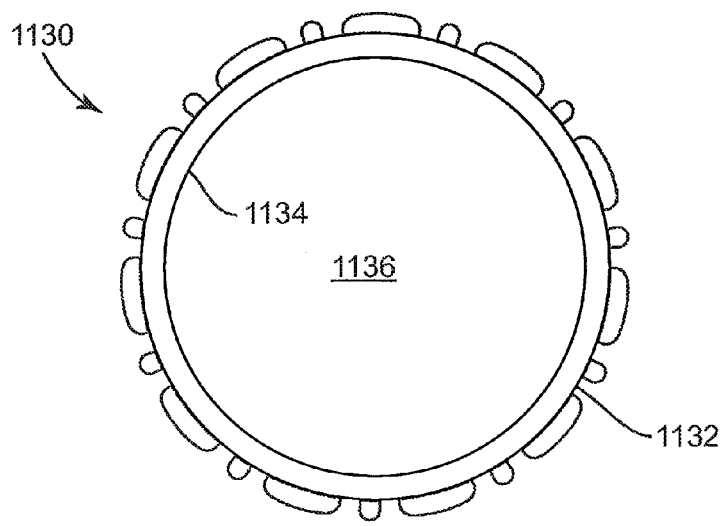
FIG. 23 is an illustration of a bottom view of the cementable hard bearing revision acetabular liner in FIG. 22 according to one aspect of the present disclosure.
Figure 24:
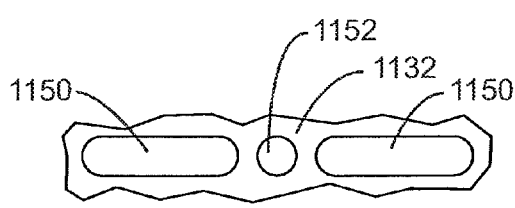
FIGS. 24 and 25 are illustrations of exemplary surface features on the cementable hard bearing revision acetabular liner of FIG. 22 according to one aspect of the present disclosure.
Figure 25:
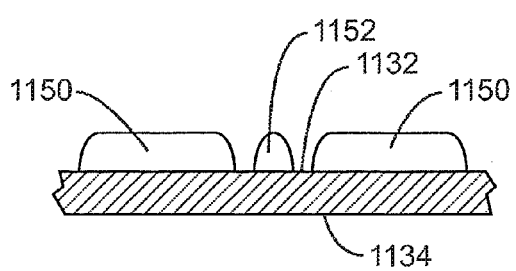

As shown in FIGS. 22 and 23, the outer facing surface 1132 is configured with surface features 1138 that promote adhesion and proper fit in the acetabular shell. In the example shown, the surface features 1138 are formed as a series of rows of alternating semi-cylindrical protrusions 1150 and dome protrusions 1152. FIGS. 24 and 25 show the exemplary surface features 1138 in greater detail. FIG. 24 shows the surface features from the top, and FIG. 25 shows the surface features from the side. As can be seen, the exemplary semi-cylindrical surface features 1150 have about an 8 mm length and a 2 mm height and width. The exemplary dome protrusions 1152 have a 2 mm diameter at their base and a 2 mm height. Although these dimensions are shown, other dimensions are contemplated. For example in some embodiments, the exemplary dome protrusions have a 1.5 mm height. Other shaped protrusions are also contemplated.

Figures 26, 27:
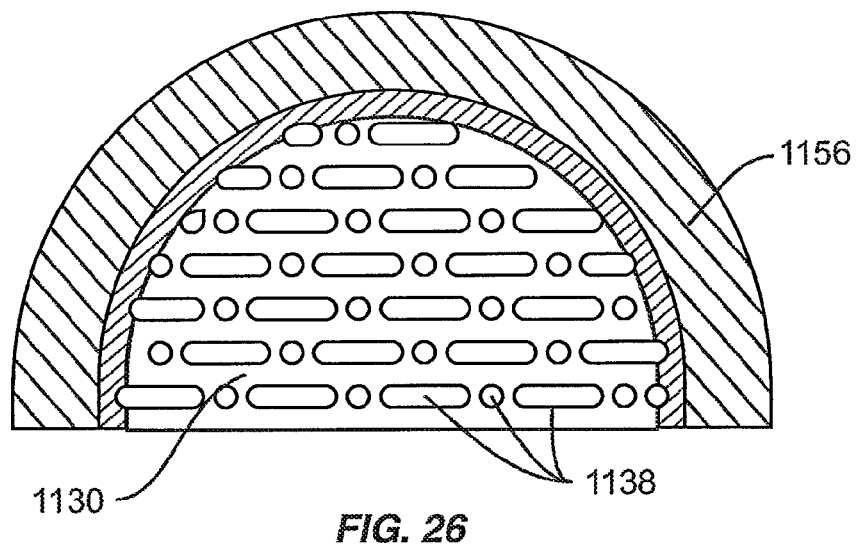
FIG. 26 is an illustration of an acetabular cup including the cementable hard bearing revision acetabular liner in FIG. 22 according to one aspect of the present disclosure.
FIG. 27 is a table showing some exemplary dimensions of an acetabular cup and ball prosthesis formed in part of the cementable hard bearing revision acetabular liner of FIG. 22 according to one aspect of the present disclosure.

FIG. 26 shows the liner 1130 in place cemented to an acetabular shell 1156. Here, the cement and the acetabular shell 1156 are shown in cross-section. As can be seen, the surface features 1138 act as an offset and as a stabilizing foundation for the liner 1130. By offsetting the liner's outer facing surface 1132 from the acetabular shell, gaps are maintained that may be filled with cement to secure the liner 1130 to the shell 1156. In addition, because the surface features 1138 interface and contact the liner, and have a consistent spacing and arrangement as shown, the surface features 1138 stabilize the liner 1130 against the cyclic loading that occurs on the acetabular cup when a patient is active. The surface features 1138 are shaped to form a radius on the liner that substantially matches the radius of the socket of the acetabular shell.

A table showing exemplary dimensional sizes for the liner, an associated femoral head, and the overall diameter of the acetabular cup is included as FIG. 27. For example, the first line of the table indicates a femoral head size of 58 mm, a liner diameter of 64 mm including the thickness of the liner body, and a cup diameter of 72 mm. The dimension of the inner liner is configured to substantially match the head dimension to provide a suitable articulating fit. In the table, the liner has body thickness of 3 mm, giving the outer facing surface of the liner a diameter of 64 mm. The surface features and cup increase the cup diameter to 72 mm. For example, the surface features 1138 may be, for example, 2 mm thick and the cup may be 2 mm thick. These dimensions are exemplary dimensions only and other dimensions are contemplated. For example, in some embodiments, the liner body has a thickness in the range of 2-4 mm thick with 2 mm surface features 1138. In other embodiments, the liner body is 4 mm thick with 2 mm surface features 1138. In yet other embodiments, the liner is 3 mm thick with 2 mm protrusions. In addition, the surface features 1138 may be either shorter or taller than 2 mm. In some examples, some of the surface features 1138 are shorter than others. For example the dome protrusions may have a height of 1.5 mm while the cylindrical protrusions have a height of 2 mm.

In use, a surgeon may initiate a revision surgery to treat a problematic previously-placed implant. In the surgery, the surgeon will commonly make an incision in the patient, and access the previously implanted acetabular cup. After cleaning the cup, and confirming a proper fit, the surgeon may insert cement directly on the outer surface 1132 of the liner 1130. The cement may then flow into the gaps between the surface features 1138. The surgeon then inserts the liner 1130 into the previously placed acetabular cup and presses the cup to further force the flowable cement between the surface features 1138, so that the surface features engage the previously placed acetabular shell. In some examples, the liner 1130 is first inserted into the cup, and the cement is injected into the gaps between the liner and the previously placed cup. In this way, the contact between the liner and the previously placed cup is assured.

While the present invention has been illustrated by the above description of embodiments, and while the embodiments have been described in some detail, it is not the intention of the applicant to restrict or in any way limit the scope of the invention to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general or inventive concept.

I claim:

1. A revision implant system for a revision surgery on a hip area of a patient, comprising:

an acetabular cup comprising a cup portion and a peripheral portion, the acetabular cup having a first surface configured to interface with the pelvic bone of the patient, the acetabular cup having a second surface facing away from the pelvic bone of the patient, at least a part of the second surface adapted to face a femoral component of a hip implant, the acetabular cup including a plurality of screw holes formed from the first surface to the second surface, the screw holes having a first diameter at the first surface and a second diameter at the second surface, the second diameter being greater than the first diameter, the plurality of screw holes having threaded inner surfaces; and a first screw having a shaft and a head, the shaft having a third diameter less than the first diameter of the screw holes, the head having a fourth diameter greater than the first diameter of the screw holes, the shaft having threads configured to engage the pelvic bone structure, the head having threads formed thereon and configured to engage the threaded inner surface of a first of the screws holes in the acetabular cup; and a second screw having a shaft and a head, the shaft of the second screw having a fifth diameter less than the first diameter of the screw holes, the head of the second screw having a sixth diameter greater than the first diameter of the screw holes, the shaft of the second screw having threads configured to engage the pelvic bone structure, the head of the second screw being free of threads to define a non-threaded head, the non-threaded head driven into secure engagement with the threaded inner surface of a second of the screw holes in the acetabular cup.

2. The revision implant system of claim 1, wherein the head of the first screw and the head of the second screw are each spherical shaped.

3. The revision implant system of claim 1, wherein the plurality of screw holes are a first plurality of screw holes formed in the peripheral portion of the acetabular cup, and wherein the acetabular cup further comprises a second plurality of screw holes formed in the cup portion and extending from a first surface of the cup portion to a second surface of the cup portion, the second plurality of screw holes having a first diameter at the first surface of the cup portion and a second diameter at the second surface of the cup portion, the second diameter being greater than the first diameter, the second plurality of screw holes having the threaded inner surfaces.

4. The revision implant system of claim 3, further comprising a revision screw having a tapered shaft and a head, the tapered shaft of the revision screw having an outer diameter less than an inner diameter of one of the second plurality of screw holes, the head of the revision screw having an outer diameter greater than the inner diameter of one of the second plurality of screw holes, the shaft of the revision screw having threads configured to engage the pelvic bone structure, and wherein the length of the revision screw is no more than twice the width of the head of the revision screw.

5. The revision implant system of claim 4, wherein the revision screw includes a thread extending about the shaft with a thread spacing between 2 mm and 4 mm.

6. The revision implant system of claim 1, further comprising a modular segmental prosthesis system for supporting the acetabular cup, the prosthesis system comprising:

an inner surface and an outer surface, the inner surface configured to interface with the pelvic bone of the patient, the outer surface facing away from the pelvic bone of the patient, a side of the system extending between the inner and outer surfaces, the side forming a cement fixation area configured to interface with the acetabular cup.

7. The modular segmental prosthesis system of claim 6, wherein the side defining the cement fixation area further comprises a plurality of spaced protrusions configured to abut against the acetabular cup with bone cement applied between the spaced protrusions and the acetabular cup to cement the prosthesis system to the acetabular cup during a surgical procedure.

8. The revision implant system of claim 1, further comprising a hard bearing liner for engagement with the acetabular cup, the acetabular cup having a socket with an inner radius, the liner being introducible into the acetabular cup in a revision surgery, the liner having an inner surface and an outer surface, the liner being sized and shaped for insertion into the inner radius of the acetabular cup, the inner surface being arranged to interface directly with a femoral ball of a prosthetic implant, the outer surface being configured to face the inner radius of the acetabular cup; and surface features formed on the outer surface of the liner and protruding from the outer surface, the surface features being configured to provide gaps therebetween for accommodating cement, the surface features forming an outer radius substantially matching the inner radius of the socket of the acetabular cup, wherein said surface features are formed as a plurality of semi-cylindrical protrusions and/or a plurality of dome protrusions.

9. The hard bearing liner of claim 8, wherein the liner is formed of a material selected from the group consisting of high carbon carbide material;

cobalt chromium and a ceramized zirconium.

10. A revision implant system for a revision surgery on a hip area of a patient, comprising:

an acetabular cup comprising a cup portion and a peripheral portion, the acetabular cup having a first surface configured to interface with the pelvic bone of the patient, the acetabular cup having a second surface facing away from the pelvic bone of the patient, at least a part of the second surface adapted to face a femoral component of a hip implant, the acetabular cup including a plurality of screw holes formed from the first surface to the second surface, the screw holes having a first diameter at the first surface and a second diameter at the second surface, the second diameter being greater than the first diameter, the plurality of screw holes having threaded inner surfaces; and a first screw having a shaft and a head, the shaft having a third diameter less than the first diameter of the screw hole, the head having a fourth diameter greater than the first diameter of the screw hole, the shaft having threads configured to engage the pelvic bone structure, the head having threads formed thereon and configured to engage the threaded inner surfaces of the screws holes in the acetabular cup;

wherein the plurality of screw holes are a first plurality of screw holes formed in the peripheral portion of the acetabular cup, and wherein the acetabular cup further comprises a second plurality of screw holes formed in the cup portion and extending from a first surface of the cup portion to a second surface of the cup portion, the second plurality of screw holes having a first diameter at the first surface of the cup portion and a second diameter at the second surface of the cup portion, the second diameter being greater than the first diameter, the second plurality of screw holes having threaded inner surfaces; and a cup hole adapter having an outer threaded surface and an inner threaded surface, the outer threaded surface being configured to engage the threads of one of the second plurality of screw holes.

11. The revision implant system of claim 10, wherein the first screw is sized such that the threads on the head of the first screw engage the threads on the inner threaded surface of the cup hole adapter.

12. A method of performing a revision surgery comprising:

introducing an the acetabular cup into a patient, the acetabular cup comprising a cup portion and a peripheral portion, the acetabular cup having a first surface configured to interface with the pelvic bone of the patient, the acetabular cup having a second surface facing away from the pelvic bone of the patient, at least a part of the second surface adapted to face a femoral component of a hip implant, the acetabular cup including a plurality of screw holes extending from the first surface to the second surface, the screw holes having a first diameter at the first surface and a second diameter at the second surface, the second diameter being greater than the first diameter, the plurality of screw holes having threaded inner surfaces;

introducing a first screw through one of the plurality of screw holes and into the pelvic bone of the patient, the first screw comprising a shaft and a head, the head of the first screw being devoid of threads to define a non-threaded head;

driving the first screw into the pelvic bone until the non-threaded head of the first screw securely engages the threaded inner surface of the one of the plurality of screw holes to capture the acetabular cup to the pelvic bone;

introducing a second screw through one of the plurality of screw holes and into the pelvic bone of the patient, the second screw comprising a shaft and a head, the shaft of the second screw having a third diameter smaller than the first diameter of the screw hole, the head of the second screw having a fourth diameter larger than the first diameter of the screw hole, the shaft of the second screw having threads configured to engage the pelvic bone structure, the head of the second screw having threads formed therein and configured to engage the threaded inner surfaces of the screws holes in the acetabular cup; and driving the second screw into the pelvic bone until the threads on the head of the second screw engage the threaded inner surface within one of the screw holes in the acetabular cup such that the cup is further secured onto the pelvic bone.

13. A revision implant system for a revision surgery on a hip area of a patient, comprising:

an acetabular cup comprising a cup portion and a peripheral portion, the acetabular cup having a first surface configured to interface with the pelvic bone of the patient, the acetabular cup having a second surface facing away from the pelvic bone of the patient, at least a part of the second surface adapted to face a femoral component of a hip implant, the acetabular cup including a plurality of screw holes formed from the first surface to the second surface, the screw holes having a first diameter at the first surface and a second diameter at the second surface, the second diameter being greater than the first diameter, the plurality of screw holes having threaded inner surfaces;

a first screw having a shaft and a head, the shaft having a third diameter less than the first diameter of the screw hole, the head having a fourth diameter greater than the first diameter of the screw hole, the shaft having threads configured to engage the pelvic bone structure, the head having threads formed thereon and configured to engage the threaded inner surfaces of the screws holes in the acetabular cup;

a hard bearing liner for engagement with the acetabular cup, the acetabular cup having a socket with an inner radius, the liner being introducible into the acetabular cup in a revision surgery, the liner having an inner surface and an outer surface, the liner being sized and shaped for insertion into the inner radius of the acetabular cup, the inner surface being arranged to interface directly with a femoral ball of a prosthetic implant, the outer surface being configured to face the inner radius of the acetabular cup; and surface features formed on the outer surface of the liner and protruding from the outer surface, the surface features being configured to provide gaps therebetween for accommodating cement, the surface features forming an outer radius substantially matching the inner radius of the socket of the acetabular cup, wherein said surface features are formed as a series of rows of alternating semi-cylindrical protrusions and dome protrusions.

14. The hard bearing liner of claim 13, wherein the semi-cylindrical protrusions have about an 8 mm length and a 2 mm height and width, and the dome protrusions have about a 2 mm diameter at their base and a 2 mm height.

* * * * *